US010287593B2

(12) United States Patent
Arai et al.

(10) Patent No.: US 10,287,593 B2
(45) Date of Patent: May 14, 2019

(54) FILAMENTOUS FUNGUS MUTANT STRAIN AND USE THEREOF

(71) Applicant: KAO CORPORATION, Chuo-ku, Tokyo (JP)

(72) Inventors: Toshiharu Arai, Wakayama (JP); Hiroshi Kakeshita, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 15/747,923

(22) PCT Filed: Jul. 28, 2016

(86) PCT No.: PCT/JP2016/072106
§ 371 (c)(1),
(2) Date: Jan. 26, 2018

(87) PCT Pub. No.: WO2017/018471
PCT Pub. Date: Feb. 2, 2017

(65) Prior Publication Data
US 2018/0216121 A1 Aug. 2, 2018

(30) Foreign Application Priority Data

Jul. 29, 2015 (JP) ................................. 2015-149729

(51) Int. Cl.
| | |
|---|---|
| *C12N 15/80* | (2006.01) |
| *C12N 1/14* | (2006.01) |
| *C13K 1/02* | (2006.01) |
| *C12P 1/02* | (2006.01) |
| *C12R 1/885* | (2006.01) |
| *C07K 14/37* | (2006.01) |
| *C12P 19/02* | (2006.01) |
| *C12P 19/14* | (2006.01) |
| *C12P 21/02* | (2006.01) |
| *C12N 9/42* | (2006.01) |
| *C12N 9/24* | (2006.01) |

(52) U.S. Cl.
CPC ............. *C12N 15/80* (2013.01); *C07K 14/37* (2013.01); *C12N 1/14* (2013.01); *C12N 9/248* (2013.01); *C12N 9/2437* (2013.01); *C12P 1/02* (2013.01); *C12P 19/02* (2013.01); *C12P 19/14* (2013.01); *C12P 21/02* (2013.01); *C12R 1/885* (2013.01); *C13K 1/02* (2013.01)

(58) Field of Classification Search
None
See application file for complete search history.

(56) References Cited

U.S. PATENT DOCUMENTS

| | | | |
|---|---|---|---|
| 6,326,477 B1 | 12/2001 | Ilmén et al. | |
| 2013/0244276 A1 | 9/2013 | Pakula et al. | |

FOREIGN PATENT DOCUMENTS

| | | |
|---|---|---|
| JP | 60-027385 A | 2/1985 |
| JP | 11-512930 A | 11/1999 |
| JP | 2010-246481 A | 11/2010 |
| JP | 2014-168424 A | 9/2014 |
| JP | 2015-039349 A | 3/2015 |
| WO | WO 2011/151515 A2 | 12/2011 |

OTHER PUBLICATIONS

International Search Report (ISR) for PCT/JP2016/072106; I.A. fd Jul. 28, 2016, dated Oct. 25, 2016 from the Japan Patent Office, Tokyo, Japan.
International Preliminary Report on Patentability (IPRP), Chapter I of the Patent Cooperation Treaty, including the Written Opinion for PCT/JP2016/072106; I.A. fd Jul. 28, 2016, dated Jan. 30, 2018, by the International Bureau of WIPO, Geneva, Switzerland.
Kondo, A et al., "Filamentous fungus, basidiomycetous enzyme," Chapter 1, in "Research Frontier of Biomass Degrading Enzymes—Focused on Cellulases and Hemicellulases," Mar. 1, 2012, ISBN 978-4-7813-0521-9, CMC Publishing Co., Ltd. pp. 10-19.
Ogasawara, W. et al., "Comparative genomic analysis of the Japanese phylogenetic tree of cellulolytic microorganism Trichoderma reesei mutants," Biosci Biotech Biochem 50 (8): 592-599 (2012), Taylor & Francis, Abingdon, UK.
Amore, A et al., "Regulation of cellulase and hemicellulase gene expression in fungi," Curr Genomics. Jun. 2013;14(4):230-49. doi: 10.2174/1389202911314040002, Bentham Science, Boca Raton, FL.
Saloheimo, M et al., "The cargo and the transport system: secreted proteins and protein secretion in *Trichoderma reesei* (*Hypocrea jecorina*)," Microbiology. Jan. 2012;158(Pt 1):46-57. doi: 10.1099/mic.0.053132-0. Epub Nov. 3, 2011, Microbiology Society, London, England.
Sato, R, "Fatty acid Metabolism and SREBP," Oreosaiensu (Oleo science) 2001, 1(11), 1065-1072, Japan Oil Chemists' Society, Tokyo, Japan.
Bien, CM et al., "Sterol regulatory element binding proteins in fungi: hypoxic transcription factors linked to pathogenesis," Eukaryot Cell. Mar. 2010;9(3):352-9. doi: 10.1128/EC.00358-09. Epub Jan. 29, 2010, American Society for Microbiology, Washington, DC.
Qin, L, "Disruption of SREBP pathway results in hyper-secretion of cellulases in filamentous fungi," Annual Meeting and Exhibition, Society for Industrial Microbiology & Biotechnology, Philadelphia, PA, Aug. 2-6, 2015, Abstract p. 63.
Willger, SD et al., "A sterol-regulatory element binding protein is required for cell polarity, hypoxia adaptation, azole drug resistance, and virulence in *Aspergillus fumigatus*," PLoS Pathog. Nov. 2008;4(11):e1000200. doi: 10.1371/journal.ppat.1000200. Epub Nov. 7, 2008, 18 pages.

(Continued)

*Primary Examiner* — Catherine S Hibbert
(74) *Attorney, Agent, or Firm* — Sterne, Kessler, Goldstein & Fox P.L.L.C.

(57) ABSTRACT

A filamentous fungus mutant strain in which enzyme production inhibition caused by glucose is suppressed is constructed, and a method of producing a polysaccharide-degrading enzyme, a method of producing a saccharide from biomass, and a method of saccharifying biomass, each using the filamentous fungus, are provided. The filamentous fungus mutant strain in which Sre1 expression is reduced compared to a parent strain or is lost.

20 Claims, 2 Drawing Sheets
Specification includes a Sequence Listing.

(56) References Cited

OTHER PUBLICATIONS

Le Crom, S et al, "Tracking the roots of cellulase hyperproduction by the fungus *Trichoderma reesei* using massively parallel DNA sequencing," Proc Natl Acad Sci U S A. Sep. 22, 2009;106(38):16151-6, and Supporting Information (11 pages), doi: 10.1073/pnas. 0905848106. Epub Sep. 2, 2009, National Acad. Sci., Washington, DC.

Vitikainen, M et al., Array comparative genomic hybridization analysis of *Trichoderma reesei* strains with enhanced cellulase production properties, BMC Genomics. Jul. 19, 2010;11:441. doi: 10.1186/1471-2164-11-441, BioMed Central, London, England.

Database GenBank [online]., Accession No. EGR47355, https://www.ncbi.nlm.nih.gov/protein/340517109?sat=37&satkey=263957827 Mar. 14, 2015 uploaded, [retrieved on Oct. 13, 2016], Martinex, D. et al., Definition: predicted protein [Trichoderma reesei QM6a].

Reilly, MC et al, "Deletion of homologs of the SREBP pathway results in hyper-production of cellulases in *Neurospora crassa* and *Trichoderma reesei*," Biotechnology for Biofuels 8:121, publised Aug. 19, 2015, BioMed Central, London, England.

SEQUENCE LISTING

<160> NUMBER OF SEQ ID NOS: 12

<210> SEQ ID NO 1
<211> LENGTH: 2568
<212> TYPE: DNA
<213> ORGANISM: Trichoderma reesei -continued

```
<220> FEATURE:
<221> NAME/KEY: CDS
<222> LOCATION: (1)..(2568)

<400> SEQUENCE: 1 atg ccc cct cat ctt cag tac ggc tca ccc aag agc gct tcg agc ccg       48
Met Pro Pro His Leu Gln Tyr Gly Ser Pro Lys Ser Ala Ser Ser Pro
1               5                   10                  15 gac tcg gcc aag gcg gga gcc gcc tcg tcg ccg gac gtc tcc agc ggc       96
Asp Ser Ala Lys Ala Gly Ala Ala Ser Ser Pro Asp Val Ser Ser Gly
            20                  25                  30 tcc cag aag gac tcg cgc aag cgc aag att tcc acc gac gac ctc gac      144
Ser Gln Lys Asp Ser Arg Lys Arg Lys Ile Ser Thr Asp Asp Leu Asp
        35                  40                  45 gat gat gat ctt ctc gag gag ggc ggg aag ccc gtc aag aag acg gct      192
Asp Asp Asp Leu Leu Glu Glu Gly Gly Lys Pro Val Lys Lys Thr Ala
50                  55                  60 cac aac atg att gag aag cgg tat cgg acc aac atc aac gac aag att      240
His Asn Met Ile Glu Lys Arg Tyr Arg Thr Asn Ile Asn Asp Lys Ile
65                  70                  75                  80 gcc gcc ctg cgt gac agc gtc ccc agc ctg cgc atc atg agc aaa agc      288
Ala Ala Leu Arg Asp Ser Val Pro Ser Leu Arg Ile Met Ser Lys Ser
                85                  90                  95 gct aga gga gaa gac aca acg gaa gat cgt gag gaa ctt cac ggc ctc      336
Ala Arg Gly Glu Asp Thr Thr Glu Asp Arg Glu Glu Leu His Gly Leu
            100                 105                 110 acg ccc gct cac aag ctt aac aaa gcc act gtg ttg agc aaa gcg acg      384
Thr Pro Ala His Lys Leu Asn Lys Ala Thr Val Leu Ser Lys Ala Thr
        115                 120                 125 gaa tat ata cga cat ctg gag aag aga aat aat cga ttg ata gac gaa      432
Glu Tyr Ile Arg His Leu Glu Lys Arg Asn Asn Arg Leu Ile Asp Glu
130                 135                 140 aac agc gcc atg cat cag aga atc gcc gca ttc gag aag ctg ttc atg      480
Asn Ser Ala Met His Gln Arg Ile Ala Ala Phe Glu Lys Leu Phe Met
145                 150                 155                 160 gcg ggt gcc atg aat ggg tcc atg aac ggc tct gtg cct ccc atg cag      528
Ala Gly Ala Met Asn Gly Ser Met Asn Gly Ser Val Pro Pro Met Gln
                165                 170                 175 cag cct acc ccg aca cag tat ccc cag gac ggc caa aca cca cag caa      576
Gln Pro Thr Pro Thr Gln Tyr Pro Gln Asp Gly Gln Thr Pro Gln Gln
            180                 185                 190 tca cag cag cag cag cag cag cag cta tcg caa atg gca ccg tct cca      624
Ser Gln Gln Gln Gln Gln Gln Gln Leu Ser Gln Met Ala Pro Ser Pro
        195                 200                 205 atg gat aac cct cag gag aac aat gga atg ccg acc ggc cta atc gag      672
Met Asp Asn Pro Gln Glu Asn Asn Gly Met Pro Thr Gly Leu Ile Glu
210                 215                 220 gtc ccg gag gac atg aag cga att ctc tcc gcc cag atg aac aac cag      720
Val Pro Glu Asp Met Lys Arg Ile Leu Ser Ala Gln Met Asn Asn Gln
225                 230                 235                 240 cca tac ccc gtt cct cag cag cta ttc cgc ccc aac ccg aca gtg gtc      768
Pro Tyr Pro Val Pro Gln Gln Leu Phe Arg Pro Asn Pro Thr Val Val
                245                 250                 255 ggc cag caa cag att cga cca atg cag cag cag caa cag cag cag ggc      816
Gly Gln Gln Gln Ile Arg Pro Met Gln Gln Gln Gln Gln Gln Gln Gly
            260                 265                 270 cag cag ggc ccg cag ccg gga tgg agc gca agc ccc tat ttc ggt aag      864
Gln Gln Gly Pro Gln Pro Gly Trp Ser Ala Ser Pro Tyr Phe Gly Lys
        275                 280                 285 ctg atg gtg ggc tcg ctc gcc gga ctg atg ata ttg gag gcg gtt cgg      912
Leu Met Val Gly Ser Leu Ala Gly Leu Met Ile Leu Glu Ala Val Arg
```

```
                                                                -continued

Leu Met Val Gly Ser Leu Ala Gly Leu Met Ile Leu Glu Ala Val Arg
    290             295             300 gaa gac gaa ccc agc agc gaa gaa ccc cag ggc cgc ggc ttg ttt gct        960
Glu Asp Glu Pro Ser Ser Glu Glu Pro Gln Gly Arg Gly Leu Phe Ala
305             310             315             320 ctg ccc ctg cag ctc ttc aga cat ata ccc tct cac ctc gat gtt cga       1008
Leu Pro Leu Gln Leu Phe Arg His Ile Pro Ser His Leu Asp Val Arg
            325             330             335 ttt gcg gga tac gac gcc atc tct atc aag ttc atg ctc ctc ttt ggc       1056
Phe Ala Gly Tyr Asp Ala Ile Ser Ile Lys Phe Met Leu Leu Phe Gly
        340             345             350 ctc gtg ctg tgg gtc ttc atc ccg tcg ctg ttt tcg aga atg gac cga       1104
Leu Val Leu Trp Val Phe Ile Pro Ser Leu Phe Ser Arg Met Asp Arg
    355             360             365 aca ccc aag aag caa caa tcg gct gct gtg caa tcc gcc cct tcc ttg       1152
Thr Pro Lys Lys Gln Gln Ser Ala Ala Val Gln Ser Ala Pro Ser Leu
370             375             380 gct tcg ccc atc agc gtt cgt cgc cgc gcg tgg gag acg gcc atc caa       1200
Ala Ser Pro Ile Ser Val Arg Arg Arg Ala Trp Glu Thr Ala Ile Gln
385             390             395             400 acc gtc tgg gtg cct cat cac agc ttc ttc ctc gag gcg gct gcg ctg       1248
Thr Val Trp Val Pro His His Ser Phe Phe Leu Glu Ala Ala Ala Leu
            405             410             415 atg ctc aag acg ctc aag ctg agc gtg cgc aac gtg ttt ggc gtc cac       1296
Met Leu Lys Thr Leu Lys Leu Ser Val Arg Asn Val Phe Gly Val His
        420             425             430 gcg tat cag ctg ctg acc ggg ctg act cca gaa caa gag gtg gcc cgg       1344
Ala Tyr Gln Leu Leu Thr Gly Leu Thr Pro Glu Gln Glu Val Ala Arg
    435             440             445 gtt cgt gcg tgg gcc acg gct ctc gac gcg cag ctt acc gga gga gat       1392
Val Arg Ala Trp Ala Thr Ala Leu Asp Ala Gln Leu Thr Gly Gly Asp
450             455             460 tcc gag att tgc atg agc cgt ctg atc ctc acg ctg ctg gcg tcc gga       1440
Ser Glu Ile Cys Met Ser Arg Leu Ile Leu Thr Leu Leu Ala Ser Gly
465             470             475             480 acc gtc cct gat acc ccc agc ggc ctc atg ctc aag gca ctt cac gtc       1488
Thr Val Pro Asp Thr Pro Ser Gly Leu Met Leu Lys Ala Leu His Val
            485             490             495 cgc gtg ctc ttg tgg gac ttg agc cag aaa tgg tat cag ctg ggt ttg       1536
Arg Val Leu Leu Trp Asp Leu Ser Gln Lys Trp Tyr Gln Leu Gly Leu
        500             505             510 gtc aac tac atc gcc acc aag att gcc gaa cga cag tgg aac gcc gcc       1584
Val Asn Tyr Ile Ala Thr Lys Ile Ala Glu Arg Gln Trp Asn Ala Ala
    515             520             525 cga gac ctg aac cag aga cta acc cac cac agc ccg caa caa gac gag       1632
Arg Asp Leu Asn Gln Arg Leu Thr His His Ser Pro Gln Gln Asp Glu
530             535             540 atg tgg gag aag aag cgt gcc gag tac atg ctg ccc gat cac ctg gcc       1680
Met Trp Glu Lys Lys Arg Ala Glu Tyr Met Leu Pro Asp His Leu Ala
545             550             555             560 gtg ctc gtc gag cag gag tgc gac aag gtc ctg acg ccc gcc gtc atc       1728
Val Leu Val Glu Gln Glu Cys Asp Lys Val Leu Thr Pro Ala Val Ile
            565             570             575 cag cga gct cac aat ctc gcc ttc aac gtg gag acg act cac gac gcc       1776
Gln Arg Ala His Asn Leu Ala Phe Asn Val Glu Thr Thr His Asp Ala
        580             585             590 atc ccg att gac ggc atg gac tcg gtt gtc gac gat aca tcg att ggg       1824
Ile Pro Ile Asp Gly Met Asp Ser Val Val Asp Asp Thr Ser Ile Gly
    595             600             605
```

```
tcg ccg atg gat gcc ctc gca gcg tgg tgg tcg acg gcc aag gtg cac    1872
Ser Pro Met Asp Ala Leu Ala Ala Trp Trp Ser Thr Ala Lys Val His
    610             615                 620 gac att ctg acg acg acg cta tac gga gac gaa gcg gag ccc gac aat    1920
Asp Ile Leu Thr Thr Thr Leu Tyr Gly Asp Glu Ala Glu Pro Asp Asn
625                 630                 635                 640 gag atg atg gaa ctg gcc gtc aag gtg gca ccc atg ggc tct cgt gct    1968
Glu Met Met Glu Leu Ala Val Lys Val Ala Pro Met Gly Ser Arg Ala
                645                 650                 655 cat gct cgc gca gtc atg gct cgc tcg gtg ctc gct cat caa tcg cgc    2016
His Ala Arg Ala Val Met Ala Arg Ser Val Leu Ala His Gln Ser Arg
            660                 665                 670 ggg aag aac att gca gcc gct gtt cag gtc ctc cgc gtc gac gcc ggt    2064
Gly Lys Asn Ile Ala Ala Ala Val Gln Val Leu Arg Val Asp Ala Gly
        675                 680                 685 ggc agc agc ctc atc gat ccc atg tcc ttt gcc tgc gcc gac gcc aac    2112
Gly Ser Ser Leu Ile Asp Pro Met Ser Phe Ala Cys Ala Asp Ala Asn
    690                 695                 700 ccc ttt gcg gac cgc gca acc gcc cct ccg cct caa ccc aac agt ccc    2160
Pro Phe Ala Asp Arg Ala Thr Ala Pro Pro Pro Gln Pro Asn Ser Pro
705                 710                 715                 720 gat ccc gac ctt cag ctt tgc cta cgc tgc gcg aca gct tcg gct cat    2208
Asp Pro Asp Leu Gln Leu Cys Leu Arg Cys Ala Thr Ala Ser Ala His
                725                 730                 735 atc aag cga ttg ggt ggc cct gtt gcc agc agc aag caa tac gtc cgt    2256
Ile Lys Arg Leu Gly Gly Pro Val Ala Ser Ser Lys Gln Tyr Val Arg
            740                 745                 750 gac tcc atc gaa aag gtc att gct ttg gca acg aga aca cga atg tcc    2304
Asp Ser Ile Glu Lys Val Ile Ala Leu Ala Thr Arg Thr Arg Met Ser
        755                 760                 765 ctc ttg agt ttt aca tcg gtg atg gag gtt ctg gag cag atc ttg gct    2352
Leu Leu Ser Phe Thr Ser Val Met Glu Val Leu Glu Gln Ile Leu Ala
    770                 775                 780 cat aaa gat acc acg aac agc ttc gcg cca ctc gtc gag agt cta gcc    2400
His Lys Asp Thr Thr Asn Ser Phe Ala Pro Leu Val Glu Ser Leu Ala
785                 790                 795                 800 gcc atc ctg cgg ctt tgg atg ggc agc cct cta gca tcg caa tgc ggt    2448
Ala Ile Leu Arg Leu Trp Met Gly Ser Pro Leu Ala Ser Gln Cys Gly
                805                 810                 815 gta cct ccc gac ttg caa gac aag atg atc aac aaa tgt ctg gga att    2496
Val Pro Pro Asp Leu Gln Asp Lys Met Ile Asn Lys Cys Leu Gly Ile
            820                 825                 830 acc aag atg gtg gtg ggc atg gaa gtg gac aca ggc tat gag agc atg    2544
Thr Lys Met Val Val Gly Met Glu Val Asp Thr Gly Tyr Glu Ser Met
        835                 840                 845 acg gac gac gaa ggg ttt cga tga                                    2568
Thr Asp Asp Glu Gly Phe Arg
    850                 855
```

<210> SEQ ID NO 2
<211> LENGTH: 855
<212> TYPE: PRT
<213> ORGANISM: Trichoderma reesei

<400> SEQUENCE: 2

```
Met Pro Pro His Leu Gln Tyr Gly Ser Pro Lys Ser Ala Ser Ser Pro
1               5                   10                  15

Asp Ser Ala Lys Ala Gly Ala Ala Ser Ser Pro Asp Val Ser Ser Gly
            20                  25                  30

Ser Gln Lys Asp Ser Arg Lys Arg Lys Ile Ser Thr Asp Asp Leu Asp
```

35                  40                  45
Asp Asp Asp Leu Leu Glu Glu Gly Gly Lys Pro Val Lys Lys Thr Ala
            50                  55                  60

His Asn Met Ile Glu Lys Arg Tyr Arg Thr Asn Ile Asn Asp Lys Ile
65                  70                  75                  80

Ala Ala Leu Arg Asp Ser Val Pro Ser Leu Arg Ile Met Ser Lys Ser
            85                  90                  95

Ala Arg Gly Glu Asp Thr Thr Glu Asp Arg Glu Glu Leu His Gly Leu
            100                 105                 110

Thr Pro Ala His Lys Leu Asn Lys Ala Thr Val Leu Ser Lys Ala Thr
            115                 120                 125

Glu Tyr Ile Arg His Leu Glu Lys Arg Asn Asn Arg Leu Ile Asp Glu
            130                 135                 140

Asn Ser Ala Met His Gln Arg Ile Ala Ala Phe Glu Lys Leu Phe Met
145                 150                 155                 160

Ala Gly Ala Met Asn Gly Ser Met Asn Gly Ser Val Pro Pro Met Gln
            165                 170                 175

Gln Pro Thr Pro Thr Gln Tyr Pro Gln Asp Gly Gln Thr Pro Gln Gln
            180                 185                 190

Ser Gln Gln Gln Gln Gln Gln Leu Ser Gln Met Ala Pro Ser Pro
            195                 200                 205

Met Asp Asn Pro Gln Glu Asn Asn Gly Met Pro Thr Gly Leu Ile Glu
210                 215                 220

Val Pro Glu Asp Met Lys Arg Ile Leu Ser Ala Gln Met Asn Asn Gln
225                 230                 235                 240

Pro Tyr Pro Val Pro Gln Gln Leu Phe Arg Pro Asn Pro Thr Val Val
            245                 250                 255

Gly Gln Gln Gln Ile Arg Pro Met Gln Gln Gln Gln Gln Gln Gln Gly
            260                 265                 270

Gln Gln Gly Pro Gln Pro Gly Trp Ser Ala Ser Pro Tyr Phe Gly Lys
            275                 280                 285

Leu Met Val Gly Ser Leu Ala Gly Leu Met Ile Leu Glu Ala Val Arg
            290                 295                 300

Glu Asp Glu Pro Ser Ser Glu Glu Pro Gln Gly Arg Gly Leu Phe Ala
305                 310                 315                 320

Leu Pro Leu Gln Leu Phe Arg His Ile Pro Ser His Leu Asp Val Arg
            325                 330                 335

Phe Ala Gly Tyr Asp Ala Ile Ser Ile Lys Phe Met Leu Leu Phe Gly
            340                 345                 350

Leu Val Leu Trp Val Phe Ile Pro Ser Leu Phe Ser Arg Met Asp Arg
            355                 360                 365

Thr Pro Lys Lys Gln Gln Ser Ala Ala Val Gln Ser Ala Pro Ser Leu
            370                 375                 380

Ala Ser Pro Ile Ser Val Arg Arg Ala Trp Glu Thr Ala Ile Gln
385                 390                 395                 400

Thr Val Trp Val Pro His His Ser Phe Phe Leu Glu Ala Ala Ala Leu
            405                 410                 415

Met Leu Lys Thr Leu Lys Leu Ser Val Arg Asn Val Phe Gly Val His
            420                 425                 430

Ala Tyr Gln Leu Leu Thr Gly Leu Thr Pro Glu Gln Glu Val Ala Arg
            435                 440                 445

Val Arg Ala Trp Ala Thr Ala Leu Asp Ala Gln Leu Thr Gly Gly Asp
450                 455                 460

```
Ser Glu Ile Cys Met Ser Arg Leu Ile Leu Thr Leu Leu Ala Ser Gly
465                 470                 475                 480

Thr Val Pro Asp Thr Pro Ser Gly Leu Met Leu Lys Ala Leu His Val
            485                 490                 495

Arg Val Leu Leu Trp Asp Leu Ser Gln Lys Trp Tyr Gln Leu Gly Leu
        500                 505                 510

Val Asn Tyr Ile Ala Thr Lys Ile Ala Glu Arg Gln Trp Asn Ala Ala
            515                 520                 525

Arg Asp Leu Asn Gln Arg Leu Thr His His Ser Pro Gln Gln Asp Glu
530                 535                 540

Met Trp Glu Lys Lys Arg Ala Glu Tyr Met Leu Pro Asp His Leu Ala
545                 550                 555                 560

Val Leu Val Glu Gln Glu Cys Asp Lys Val Leu Thr Pro Ala Val Ile
                565                 570                 575

Gln Arg Ala His Asn Leu Ala Phe Asn Val Glu Thr His Asp Ala
                580                 585                 590

Ile Pro Ile Asp Gly Met Asp Ser Val Val Asp Asp Thr Ser Ile Gly
        595                 600                 605

Ser Pro Met Asp Ala Leu Ala Ala Trp Trp Ser Thr Ala Lys Val His
        610                 615                 620

Asp Ile Leu Thr Thr Thr Leu Tyr Gly Asp Glu Ala Glu Pro Asp Asn
625                 630                 635                 640

Glu Met Met Glu Leu Ala Val Lys Val Ala Pro Met Gly Ser Arg Ala
                645                 650                 655

His Ala Arg Ala Val Met Ala Arg Ser Val Leu Ala His Gln Ser Arg
                660                 665                 670

Gly Lys Asn Ile Ala Ala Val Gln Val Leu Arg Val Asp Ala Gly
                675                 680                 685

Gly Ser Ser Leu Ile Asp Pro Met Ser Phe Ala Cys Ala Asp Ala Asn
        690                 695                 700

Pro Phe Ala Asp Arg Ala Thr Ala Pro Pro Gln Pro Asn Ser Pro
705                 710                 715                 720

Asp Pro Asp Leu Gln Leu Cys Leu Arg Cys Ala Thr Ala Ser Ala His
                725                 730                 735

Ile Lys Arg Leu Gly Gly Pro Val Ala Ser Ser Lys Gln Tyr Val Arg
            740                 745                 750

Asp Ser Ile Glu Lys Val Ile Ala Leu Ala Thr Arg Thr Arg Met Ser
            755                 760                 765

Leu Leu Ser Phe Thr Ser Val Met Glu Val Leu Glu Gln Ile Leu Ala
        770                 775                 780

His Lys Asp Thr Thr Asn Ser Phe Ala Pro Leu Val Glu Ser Leu Ala
785                 790                 795                 800

Ala Ile Leu Arg Leu Trp Met Gly Ser Pro Leu Ala Ser Gln Cys Gly
                805                 810                 815

Val Pro Pro Asp Leu Gln Asp Lys Met Ile Asn Lys Cys Leu Gly Ile
            820                 825                 830

Thr Lys Met Val Val Gly Met Glu Val Asp Thr Gly Tyr Glu Ser Met
        835                 840                 845

Thr Asp Asp Glu Gly Phe Arg
850                 855

<210> SEQ ID NO 3
<211> LENGTH: 3494
```

<212> TYPE: DNA
<213> ORGANISM: Trichoderma reesei

<400> SEQUENCE: 3

```
gtaccaaccg gcctttcttc gtatgtttct gtctgtagca ctcgctctct gatattcccg      60
ctccaaagac acccccatc gtgtctgcga gcggccatcc ctggccatcc cacaccctcg      120
gcaaagcttc tcgctgggct gggtgtctgt ctcagcaaat cccgctttaa gctgtcgacc      180
cgccggtcag gcagaagggg gaaaaaacag ctgatctcat cgtactatcg ctggtgagag      240
cgtccactgc ctctgcacca ctcagtccac tttgcgtcgc cgaccgcacg atcctctgcc      300
aacaatcgag tcaccctctc accccccctt ggccagaccc tgccgcattc tcgcctggtc      360
tcagtctcga gcccgtcgtc gcctcgactc gtctcgtcga gcccggctgt cgctgcatga      420
gctgatccgc gagcgttccc ccggtctctg cagccgccag tttcacccct ccccccccct      480
ccctcaaaga acgccgtccc catggccgat gaggatggct ccaacgggct gggtttgac       540
gacccgagct tcggcttcat aggcggtggc cccgggtctc tggatggcat ctcagatgcg      600
cccatattcg gcggcgatcc ctcagccgga tacgtcgatt ctggagtctg gcagctggat      660
gcctcgcctc agtccaactc gtacgatctc ggcagcaaca ccaccctctc ctccgcccag      720
ccaggatact tgtccccgtc ctggccgacc ccgaccttgg acccccgaca gcaccagcct      780
cagcagcctc agcaacaacc gcaaccacca cagcagcagc agcagcagca acaacagcaa      840
caacaacagc agcagcagcc cgaccctacc gcctttggcc tgaccaactt cgaccctgcg      900
tcagtctact tccccggtgt agcggccacc aagcggggcg ccctcccggt gtccaagccg      960
tccctacgct cgggaaccat cctgagtcct gccatgcagg aacaactgag aaacattgcc      1020
atgccccctc atcttcagta cggctcaccc aagagcgctt cgagcccgga ctcggccaag      1080
gcgggagccg cctcgtcgcc ggacgtctcc agcggctccc agaaggactc gcgcaagcgc      1140
aagatttcca ccgacgacct cgacgatgat gatcttctcg aggagggcgg gaagcccgtc      1200
aagaagacgg ctcacaacat gattgagaag cggtatcgga ccaacatcaa cgacaagatt      1260
gccgccctgc gtgacagcgt ccccagcctg cgcatcatga gcaaaagcgc tagaggagaa      1320
gacacaacgg aagatcgtga ggaacttcac ggcctcacgc ccgctcacaa gcttaacaaa      1380
gccactgtag gaagatttcc actcagtttg attatgacaa atggggcaaa ggatgaaagg      1440
ggggaggcgt catatctcat caatgactaa ccaatgtaat aggtgttgag caaagcgacg      1500
gaatatatac gacatctgga gaagagaaat aatcgattga tagacgaaaa cagcgccatg      1560
catcagagaa tcgccgcatt cgagaagctg ttcatggcgg gtgccatgaa tgggtccatg      1620
aacggctctg tgcctcccat gcagcagcct accccgacac agtatcccca ggacggccaa      1680
acaccacagc aatcacagca gcagcagcag cagcagctat cgcaaatggc accgtctcca      1740
atggataacc ctcaggagaa caatggaatg ccgaccggcc taatcgaggt cccggaggac      1800
atgaagcgaa ttctctccgc ccagatgaac aaccagccat ccccgttcc tcagcagcta       1860
ttccgcccca acccgacagt ggtcggccag caacagattc gaccaatgca gcagcagcaa      1920
cagcagcagg gccagcaggg cccgcagccg ggatggagcg caagcccctta tttcggtaag     1980
ctgatggtgg gctcgctcgc cggactgatg atattggagg cggttcggga agacgaaccc      2040
agcagcgaag aaccccaggg ccgcggcttg tttgctctgc ccctgcagct cttcagacat      2100
ataccctctc acctcgatgt tcgatttgcg ggatacgacg ccatctctat caagttcatg      2160
ctcctctttg gcctcgtgct gtgggtcttc atcccgtcgc tgttttcgag aatggaccga      2220
```

```
acacccaaga agcaacaatc ggctgctgtg caatccgccc cttccttggc ttcgcccatc    2280
agcgttcgtc gccgcgcgtg ggagacggcc atccaaaccg tctgggtgcc tcatcacagc    2340
ttcttcctcg aggcggctgc gctgatgctc aagacgctca agctgagcgt gcgcaacgtg    2400
tttggcgtcc acgcgtatca gctgctgacc gggctgactc cagaacaaga ggtggcccgg    2460
gttcgtgcgt gggccacggc tctcgacgcg cagcttaccg gaggagattc cgagatttgc    2520
atgagccgtc tgatcctcac gctgctgcg tccggaaccg tccctgatac ccccagcggc    2580
ctcatgctca aggcacttca cgtccgcgtg ctcttgtggg acttgagcca gaaatggtat    2640
cagctgggtt tggtcaacta catcgccacc aagattgccg aacgacagtg gaacgccgcc    2700
cgagacctga accagagact aacccaccac agcccgcaac aagacgagat gtgggagaag    2760
aagcgtgccg agtacatgct gcccgatcac ctggccgtgc tcgtcgagca ggagtgcgac    2820
aaggtcctga cgcccgccgt catccagcga gctcacaatc tcgccttcaa cgtggagacg    2880
actcacgacg ccatcccgat tgacggcatg gactcggttg tcgacgatac atcgattggg    2940
tcgccgatgg atgccctcgc agcgtggtgg tcgacggcca aggtgcacga cattctgacg    3000
acgacgctat acgagacga agcggagccc gacaatgaga tgatggaact ggccgtcaag    3060
gtggcaccca tgggctctcg tgctcatgct cgcgcagtca tggctcgctc ggtgctcgct    3120
catcaatcgc gcgggaagaa cattgcagcc gctgttcagg tcctccgcgt cgacgccggt    3180
ggcagcagcc tcatcgatcc catgtccttt gcctgcgccg acgccaaccc ctttgcggac    3240
cgcgcaaccg cccctccgcc tcaacccaac agtcccgatc ccgaccttca gctttgccta    3300
cgctgcgcga cagcttcggc tcatatcaag cgattgggtg gccctgttgc cagcagcaag    3360
caatacgtcc gtgactccat cgaaaaggtc attgctttgg caacgagaac acgaatgtcc    3420
ctcttgagtt ttacatcggt gatggaggtt ctggagcaga tcttggctca taaagatacc    3480
acgaacagct cgc                                                      3494

<210> SEQ ID NO 4
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 4
cgtttccagt gcgcattacc ggaggagatt ccgag                                35

<210> SEQ ID NO 5
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 5
ccaatgatgt gcgcaggcaa tgtttctcag ttgtt                                35

<210> SEQ ID NO 6
<211> LENGTH: 3089
<212> TYPE: DNA
<213> ORGANISM: Aspergillus nidurans

<400> SEQUENCE: 6
tgcgcacatc attggatagg cagattactc agcctgaatg acatcaacat gttacccatg     60
atacaatagg tcacacaaac aagcgctaag atgcacttgg tatgacaagc ccagtagtcc    120
```

```
gtttcaaaag acctagatga tgaactacaa catgaggtgt tgcctcctga tccagtccaa    180
ctgcaaacgc tgatgtatac tcaatcaagc ctgatgtaaa tgctgcgact cgattcgctg    240
gatatgaaga tcaaagagag ctctgatggg tccaatatag ccgggttttg ttaggacagt    300
ccaccacacc gatattagaa ttggtcaagc accttatcat ttcatagaga ttgcggtttc    360
tagatctacg ccaggaccga gcaagcccag atgagaaccg acgcagattt ccttggcacc    420
tgttgcttca gctgaatcct ggcaatacga gatacctgct tgaatatttt tgaatagctc    480
gcccgctgga gagcatcctg aatgcaagta acaaccgtag aggctgacac ggcaggtgtt    540
gctagggagc gtcgtgttct acaaggccag acgtcttcgc ggttgatata tatgtatgtt    600
tgactgcagg ctgctcagcg acgacagtca agttcgccct cgctgcttgt gcaataatcg    660
cagtggggaa gccacaccgt gactcccatc tttcagtaaa gctctgttgg tgtttatcag    720
caatacacgt aatttaaact cgttagcatg gggctgatag cttaattacc gtttaccagt    780
gccgcggttc tgcagctttc cttggcccgt aaaattcggc gaagccagcc aatcaccagc    840
taggcaccag ctaaacccta taattagtct cttatcaaca ccatccgctc ccccgggatc    900
aatgaggaga atgaggggga tgcggggcta agaagcctaa cataaccctc atgccaactc    960
ccagtttaca ctcgtcgagc caacatcctg actataagct aacacagaat gcctcaatcc   1020
tgggaagaac tggccgctga taagcgcgcc cgcctcgcaa aaaccatccc tgatgaatgg   1080
aaagtccaga cgctgcctgc ggaagacagc gttattgatt cccaaagaa atcggggatc   1140 cttttcagagg ccgaactgaa gatcacagag gcctccgctg cagatcttgt gtccaagctg   1200
gcggccggag agttgacctc ggtggaagtt acgctagcat tctgtaaacg ggcagcaatc   1260
gcccagcagt tagtagggtc ccctctacct ctcagggaga tgtaacaacg ccaccttatg   1320
ggactatcaa gctgacgctg gcttctgtgc agacaaactg cgcccacgag ttcttccctg   1380
acgccgctct cgcgcaggca agggaactcg atgaatacta cgcaaagcac aagagacccg   1440
ttggtccact ccatggcctc cccatctctc tcaaagacca gcttcgagtc aaggtacacc   1500
gttgccccta gtcgttaga tgtcccttttt tgtcagctaa catatgccac cagggctacg   1560
aaacatcaat gggctacatc tcatggctaa acaagtacga cgaaggggac tcggttctga   1620
caaccatgct ccgcaaagcc ggtgccgtct tctacgtcaa gacctctgtc ccgcagaccc   1680
tgatggtctg cgagacagtc aacaacatca tcgggcgcac cgtcaaccca cgcaacaaga   1740
actggtcgtg cggcggcagt tctggtggtg agggtgcgat cgttgggatt cgtggtggcg   1800
tcatcggtgt aggaacggat atcggtggct cgattcgagt gccggccgcg ttcaacttcc   1860
tgtacggtct aaggccgagt catgggcggc tgccgtatgc aaagatggcg aacagcatgg   1920
agggtcagga gacggtgcac agcgttgtcg ggccgattac gcactctgtt gagggtgagt   1980
ccttcgcctc ttccttcttt tcctgctcta taccaggcct ccactgtcct cctttcttgc   2040
tttttatact atatacgaga ccggcagtca ctgatgaagt atgttagacc tccgcctctt   2100
caccaaatcc gtcctcggtc aggagccatg gaaatacgac tccaaggtca tccccatgcc   2160
ctggcgccag tccgagtcgg acattattgc ctccaagatc aagaacgcg ggctcaatat   2220 cggctactac aacttcgacg gcaatgtcct tccacaccct cctatcctgc gcggcgtgga   2280
aaccaccgtc gccgcactcg ccaaagccgg tcacaccgtg accccgtgga cgccatacaa   2340
gcacgatttc ggccacgatc tcatctccca tatctacgcg gctgacggca cgccgacgt   2400 aatgcgcgat atcagtgcat ccggcgagcc ggcgattcca aatatcaaag acctactgaa   2460
```

-continued

```
cccgaacatc aaagctgtta acatgaacga gctctgggac acgcatctcc agaagtggaa    2520
ttaccagatg gagtaccttg agaaatggcg ggaggctgaa gaaaaggccg ggaaggaact    2580
ggacgccatc atcgcgccga ttacgcctac cgctgcggta cggcatgacc agttccggta    2640
ctatgggtat gcctctgtga tcaacctgct ggatttcacg agcgtggttg ttccggttac    2700
ctttgcggat aagaacatcg ataagaagaa tgagagtttc aaggcggtta gtgagcttga    2760
tgccctcgtg caggaagagt atgatccgga ggcgtaccat ggggcaccgg ttgcagtgca    2820
ggttatcgga cggagactca gtgaagagag gacgttggcg attgcagagg aagtggggaa    2880
gttgctggga aatgtggtga ctccatagct aataagtgtc agatagcaat ttgcacaaga    2940
aatcaatacc agcaactgta aataagcgct gaagtgacca tgccatgcta cgaaagagca    3000
gaaaaaaacc tgccgtagaa ccgaagagat atgacacgct tccatctctc aaaggaagaa    3060
tcccttcagg gttgcgtttc cagtgcgca                                      3089
```

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
tgcgcacatc attggatagg                                                20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
tgcgcactgg aaacgcaacc                                                20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
atccctcccc catcgtcgca                                                20

<210> SEQ ID NO 10
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 10
tcctgaccct ccatgctgtt cgccatcttt                                     30

<210> SEQ ID NO 11
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 11

```
ccagtccgag tcggaca                                                        17

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
cattgtatgc ctgataccac                                                     20
```

FILAMENTOUS FUNGUS MUTANT STRAIN AND USE THEREOF

FIELD OF THE INVENTION

The present invention relates to a filamentous fungus mutant strain and production of a polysaccharide-degrading enzyme using the filamentous fungus.

BACKGROUND OF THE INVENTION

Biomass refers to renewable organic resources of biological origin, excluding fossil resources. In particular, cellulosic biomass is attracting attention. Being developed all over the world are technologies of degrading cellulose into saccharides and producing useful resources, such as alternatives for petroleum resources and biofuel, from the resulting saccharides by chemical conversion or fermentation technology using microorganisms.

Cellulosic biomass is mainly composed of cellulose, hemicellulose, and lignin. Such biomass is known to be degraded in a complicated form by synergistic action of, for example, a cellulase degrading cellulose and a hemicellulase degrading hemicellulose. Efficient utilization of cellulosic biomass needs to develop a saccharification enzyme capable of highly efficiently degrading cellulose and hemicellulose.

In order to efficiently degrade cellulose to glucose, the above-mentioned various cellulases are required to comprehensively function. In addition, since xylan is a polysaccharide which is contained in plants in a large amount next to cellulose, filamentous fungi, such as *Trichoderma*, producing various cellulases and xylanases have attracted attention as bacteria degrading plant saccharides (Non Patent Literature 1).

In particular, *Trichoderma* can simultaneously produce a cellulase and a xylanase and also produces a large amount of complexing enzymes thereof and has been therefore investigated as a host for cellulase production (Non Patent Literature 2).

However, in order to industrially produce a cellulase and a xylanase with filamentous fungi, it is necessary to develop a technology for inexpensive mass production and to produce a further productive strain.

For example, Avicel, which is microcrystalline cellulose, is generally used for production of cellulase, but it is expensive and is difficult to be used in industrial application from the viewpoint of cost. In addition, since many of cellulose substrates are insoluble, inexpensive and soluble carbon sources, such as glucose, are desirable to be used also from the viewpoint of load on the industrial process. However, culture using glucose is known to cause a reduction or saturation in productivity by a control mechanism called catabolite repression. It is known that, for example, in *Aspergillus* filamentous fungi, wide-area control transcription factors, such as CreA, CreB, CreC, and CreD, are involved in the catabolite repression (Patent Literatures 1 and 2). It is believed that the catabolite repression can be regulated by controlling these factors, but avoidance of glucose inhibition is conceived to be still insufficient. Mechanism analysis has been developed also in *Trichoderma* (Patent Literature 3 and Non Patent Literature 3), but many functionally unclear points still remain, and avoidance of glucose inhibition has not been achieved also in *Trichoderma*.

Incidentally, a protein secreted by a filamentous fungus (mold) is also believed to be transferred from endoplasmic reticulum to cell membrane through the Golgi apparatus by secretory vesicles and then to the outside of the cell, as in other eukaryotic cells. The protein, such as a secreted enzyme, to be secreted to the outside of the cell first passes through the endoplasmic reticulum membrane while being synthesized on the endoplasmic reticulum membrane and is subjected to an appropriate folding or glycosylation in the endoplasmic reticulum. The protein then moves to the Golgi apparatus for further glycosylation and is then collected in secretory vesicles and is transferred cytoskeleton-dependently to the cell membrane. The protein is transferred by fusion of the secretory vesicles with the cell membrane and moves to the outside of the cell (Non Patent Literature 4). In order to correctly transfer a target protein, every process of the transfer is important, and the lack of the mechanism in each transport process can be an obstacle to the protein transport.

As one of gene expression control mechanisms using protein transport pathways, a transcription factor called sterol regulatory element binding protein (SREBP) is known. In an SREBP pathway regulating the gene expression of cholesterol synthesis enzymes, SREBP1 (also called Sre1 or SreA) forms a complex with an SREBP cleavage-activating protein and is transported from the endoplasmic reticulum to the Golgi apparatus. It is known that the SREBP is subjected to splicing on the Golgi apparatus as the destination and the activated SREBP remigrates into the nucleus to control the expression of the genes involved in a sterol synthesis pathway or a fatty acid or neutral lipid synthesis pathway (Non Patent Literature 5).

It has been reported that in fungi, the SREBP pathway is involved in pathogenicity or hypoxic response (Non Patent Literature 6), but the details thereof are not known. It has been recently reported that in *Trichoderma*, destruction of the SREBP pathway increases the productivity of a cellulase (Non Patent Literature 7), but the details of the relation between the SREBP pathway and the increase in the cellulase productivity are unclear.

[Patent Literature 1] JP-A-2014-168424
[Patent Literature 2] JP-A-2015-39349
[Patent Literature 3] JP-A-H11-512930
[Non Patent Literature]
  [Non Patent Literature 1] Akihiko Kondo, Yoshihiko Amano, and Yutaka Tamaru, "Baiomasu Bunkai Koso Kenkyu no Saizensen (Research Frontier of Biomass Degrading Enzymes—Focused on Cellulases and Hemicellulases—", CMC Publishing Co., Ltd. pp. 10-19
  [Non Patent Literature 2] Wataru Ogasawara and Yosuke Shida, "Kagaku to Seibutsu (Chemistry and Biology)", Vol. 50, The Japan Society for Bioscience, Biotechnology, and Agrochemistry, Vol. 50, No. 8, pp. 592-599, 2012, August
  [Non Patent Literature 3] Amore A1, Giacobbe S, Faraco V., Curr Genomics, 2013, June, 14(4): 230-49
  [Non Patent Literature 4] Saloheimo M1, Pakula T M., Microbiology, 2012, January, 158 (Pt 1): 46-57
  [Non Patent Literature 5] Ryuichiro Sato, "Oleoscience 2001", Vol. 1, No. 11, pp. 1065-1072
  [Non Patent Literature 6] Clara M. Bien and Peter J. Espenshade, EUKARYOTIC CELL, 9(3), 352-359 (2010)
  [Non Patent Literature 7] Dr. Lina Qin et al., "P63 Disruption of SREBP pathway results in hyper-secretion of cellulases in Filamentous fungi", SIMB (Society for Industrial Microbiology & Biotechnology), Annual Meeting and Exhibition, https://sim.confex.com/sim/2015/webprogram/Paper30506.html

SUMMARY OF THE INVENTION

The present invention relates to:

[1] A filamentous fungus mutant strain wherein Sre1 expression is reduced compared to a parent strain or is lost;

[2] A method of producing a cellulase and/or a xylanase, the method comprising a step of culturing the filamentous fungus mutant strain according to aspect [1] in the presence of a cellulase inducer to generate and accumulate a cellulase and/or a xylanase in a culture product, and a step of collecting the cellulase and/or the xylanase from the culture product;

[3] A method of producing a cellulase and/or a xylanase, the method comprising a step of culturing the filamentous fungus mutant strain according to aspect [1] in the presence of a cellulase inducer and glucose to generate and accumulate a cellulase and/or a xylanase in a culture product, and a step of collecting the cellulase and/or the xylanase from the culture product;

[4] A method of producing a saccharide from biomass, the method comprising using a culture product, obtained by culturing the filamentous fungus mutant strain according to aspect [1] in the presence of a cellulase inducer, as a biomass saccharifying agent; and

[5] A method of saccharifying biomass, the method comprising using a culture product, obtained by culturing the filamentous fungus mutant strain according to aspect [1] in the presence of a cellulase inducer, as a biomass saccharifying agent.

DETAILED DESCRIPTION OF THE INVENTION

Figure 1:
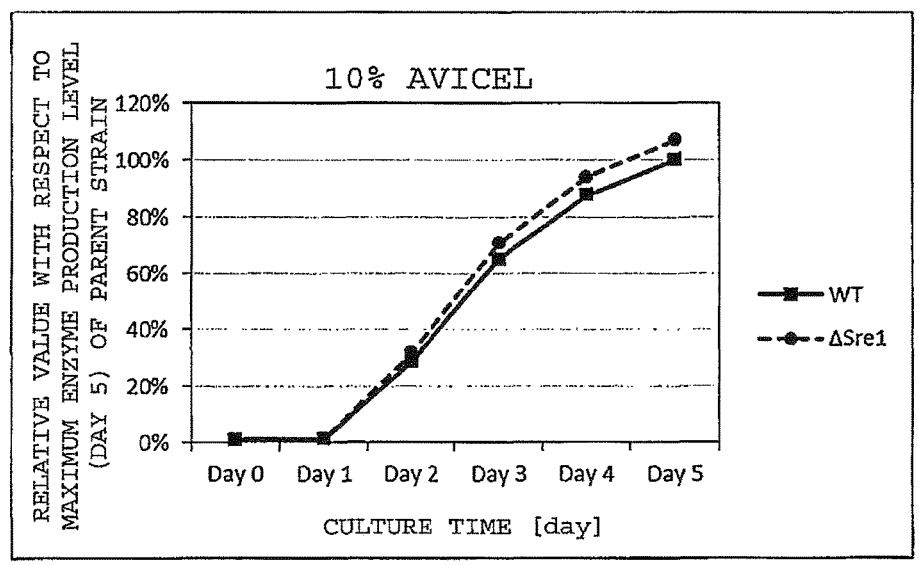
FIG. 1 is a graph showing protein productivity when cellulase expression of *Trichoderma reesei* was induced with Avicel. The solid line connecting black squares indicates PCD-10 strain, and the broken line connecting black circles indicates ΔSre1 strain.
Figure 2:
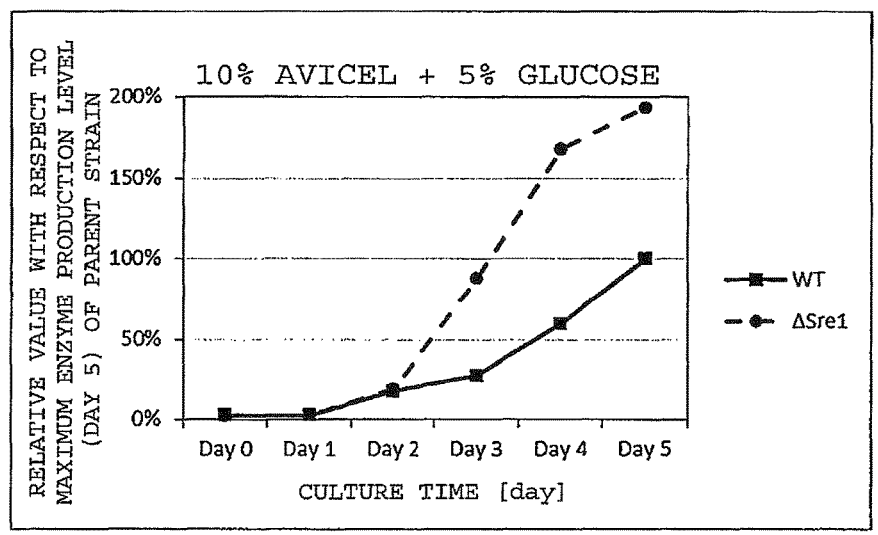
FIG. 2 is a graph showing protein productivity when the culture was performed in the presence of 5% glucose in addition to Avicel. The solid line connecting black squares indicates PCD-10 strain, and the broken line connecting black circles indicates ΔSre1 strain.

The present invention constructs a filamentous fungus mutant strain in which enzyme production inhibition caused by glucose is suppressed and provides a method of producing a polysaccharide-degrading enzyme, a method of producing a saccharide from biomass, and a method of saccharifying biomass, each using the filamentous fungus.

The present inventors diligently studied to solve the above-described problems and, as a result, found that glucose inhibition in the production of a cellulase or a xylanase is dramatically suppressed in a filamentous fungus mutant strain that has lost the expression of Serf involved in transcription regulation of genes encoding cholesterol synthesis enzymes and the strain is useful as filamentous fungi for producing the enzyme, and the present invention was accomplished.

The present invention provides filamentous fungi in which enzyme production inhibition caused by glucose is suppressed in the production of a cellulase or a xylanase, and enables production of a cellulase and/or a xylanase by using the filamentous fungi even under culture conditions including a high concentration of glucose. Furthermore, a saccharide can be produced by saccharifying biomass by using the filamentous fungi.

In the present specification, amino acid sequence and nucleotide sequence identities are calculated according to a Lipman-Pearson method (Lipman, D. J., Pearson, W. R.: Science, 1985, 227: 1435-1441). Specifically, the identity is calculated by performing analysis using a homology analysis (Search homology) program of genetic information processing software Genetyx-Win (Software Development Co.) and setting the unit size to compare (ktup) at 2.

In the present specification, "one or several" used in connection with deletion, substitution, addition, or insertion of amino acid(s) or nucleotide(s) in an amino acid sequence or a nucleotide sequence can be, for example, 1 to 12, preferably 1 to 8, more preferably 1 to 4, unless otherwise defined. In the present specification, the term "addition" of amino acid(s) or nucleotide(s) includes addition of one or several amino acids or nucleotides to one end or both ends of a sequence.

In the present specification, the term "stringent conditions" relating to hybridization refers to conditions allowing a gene comprising a nucleotide sequence having a sequence identity of about 80% or more or about 90% or more to be verified, unless otherwise defined. Examples of the "stringent conditions" include the conditions described in Molecular Cloning: A LABORATORY MANUAL THIRD EDITION (Joseph Sambrook, David W. Russell, Cold Spring Harbor Laboratory Press, 2001). A person skilled in the art of hybridization can appropriately make stringent conditions by regulating, for example, the salt concentration of a hybridization solution and the temperature, depending on, for example, the nucleotide sequence, the concentration and the length of a probe. In one example, the "stringent conditions" are preferably 5×SSC and 70° C. or more, more preferably 5×SSC and 85° C. or more for hybridization condition; and preferably 1×SSC and 60° C. or more, more preferably 1×SSC and 73° C. or more for washing condition. The above-mentioned combinations of SSC and temperature conditions are merely examples, and a person skilled in the art can achieve appropriate stringency by appropriately combining the above-mentioned or other factors determining the stringency of hybridization.

In the present specification, the terms "upstream" and "downstream" of a gene refer to a region extending toward the 5' end and the 3' end, respectively, of a targeted gene or region. The upstream and the downstream of a gene are not limited to the upstream region and the downstream region from the translation initiation site of the gene, unless otherwise defined.

<Construction of Filamentous Fungus Mutant Strain>

In the filamentous fungus mutant strain of the present invention, the Sre1 expression is reduced compared to a parent strain or is lost.

"Sre1" is a protein having the amino acid sequence represented by SEQ ID NO: 2 and is a transcription factor for genes encoding cholesterol synthesis enzymes. The protein has HLH Superfamily and DUF2014 Superfamily domains and therefore corresponds to Sre1 registered in the NCBI database as Sterol regulatory element-binding protein 1. The protein has an amino acid sequence identity with other Sre1s, i.e., with Sre1 derived from *Fusarium oxysporum* f. sp. cubense race 1 of 58% and with Sre1 derived from *Acremonium chrysogenum* ATCC 11550 of 55%.

Examples of Sre1 in the present invention include:
(a) a protein having the amino acid sequence represented by SEQ ID NO: 2;

(b) a protein having the amino acid sequence represented by SEQ ID NO: 2 in which one to several amino acids are deleted, substituted, added or inserted and having an activity as a transcription factor for genes encoding cholesterol synthesis enzymes; and (c) a protein having an amino acid sequence with an identity of 80% or more with the amino acid sequence represented by SEQ ID NO: 2 and having an activity as a transcription factor for genes encoding cholesterol synthesis enzymes.

Examples of the amino acid sequence having an identity of 80% or more with the amino acid sequence represented by SEQ ID NO: 2 include amino acid sequences preferably having an identity of 90% or more, more preferably 95% or more, even more preferably 97% or more, even more preferably 98% or more, even more preferably 99% or more.

In the present invention, the "expression" of Sre1 means that a translation product (i.e., Sre1 protein (referred to as "Sre1")) is produced from the gene encoding the protein (sre1 gene) and is localized at the site of action in a functional state. A reduction in Sre1 expression means a state where the amount of Sre1 protein present in the filamentous fungus mutant strain cells is significantly reduced compared to that in the parent strain resultantly. Accordingly, the way for reducing or losing the Sre1 expression in the filamentous fungus mutant strain of the present invention encompasses modifications of genetic level, transcriptional level, posttranscriptional regulatory level, translational level, and posttranslational modification level.

"A reduction in Sre1 expression compared to a parent strain" means that the amount of Sre1 expressed in filamentous fungi is reduced compared to a parent strain, more specifically, the amount of Sre1 expressed in the cells is usually reduced to 50% or less, preferably 20% or less, more preferably 10% or less compared to a parent strain, and thereby the activity is similarly reduced. It is most preferred that the amount of Sre1 expressed is 0%, that is, the Sre1 expression is lost.

The comparison of amount of Sre1 expressed is performed based on the amount of the Sre1 protein expressed.

The amount of Sre1 expressed can be measured by a known immunological method, such as western blotting or immunohistochemical staining.

The filamentous fungus mutant strain in which Sre1 expression is reduced compared to a parent strain or is lost preferably can be acquired by deleting or inactivating the sre1 gene on the chromosomal DNA of the filamentous fungus parent strain. Herein, the sre1 gene refers to a DNA having the transcriptional region including an ORF and transcriptional regulatory regions such as a promoter of the gene.

In the present invention, the sre1 gene specifically includes a gene having an ORF given by any of the following polynucleotides:

(d) a polynucleotide having the nucleotide sequence represented by SEQ ID NO: 1;

(e) a polynucleotide having a nucleotide sequence with an identity of 80% or more, preferably 85% or more, more preferably 90% or more, even more preferably 95% or even more, more preferably 96% or more, even more preferably 97% or more, even more preferably 98% or more, even more preferably 99% or more with the nucleotide sequence represented by SEQ ID NO: 1 and encoding a protein having an activity as a transcription factor for genes encoding cholesterol synthesis enzymes;

(f) a polynucleotide hybridizing to a complementary strand of the polynucleotide having the nucleotide sequence represented by SEQ ID NO: 1 under stringent conditions and encoding a protein having an activity as a transcription factor for genes encoding cholesterol synthesis enzymes;

(g) a polynucleotide encoding a protein having the amino acid sequence represented by SEQ ID NO: 2;

(h) a polynucleotide encoding a protein having the amino acid sequence represented by SEQ ID NO:2 in which one to several amino acids are deleted, substituted, added or inserted and having an activity as a transcription factor for genes encoding cholesterol synthesis enzymes; and (i) a polynucleotide encoding a protein having an amino acid sequence with an identity of 80% or more, preferably 85% or more, more preferably 90% or more, even more preferably 95% or more, even more preferably 96% or more, even more preferably 97% or more, even more preferably 98% or more, even more preferably 99% or more with the amino acid sequence represented by SEQ ID NO: 2 and having an activity as a transcription factor for genes encoding cholesterol synthesis enzymes.

Examples of deletion or inactivation of the sre1 gene include introducing a mutation into one or more nucleotides on the nucleotide sequence of the gene, that is, deleting a part or the whole of the nucleotide sequence of the gene, or substituting for or inserting to the nucleotide sequence, another nucleotide sequence, (in this case, the amino acid sequence of Sre1 may be the same as or different from that of a parent strain).

Examples of the nucleotide region into which a mutation is introduced include the transcriptional region of the sre1 gene and transcriptional regulatory regions, such as a promoter and an enhancer (transcriptional activation region), of the gene, and preferred is the transcriptional region.

Examples of the transcriptional regulatory region of the sre1 gene include a region of 30 nucleotides upstream of the 5' end of the transcriptional region of the sre1 gene on the chromosomal DNA. Examples of the transcriptional activation region of the sre1 gene include a region corresponding to the nucleotides −1000 to −500 upstream.

A nucleotide mutation may be introduced into the transcriptional region without limitation of the kinds and number of nucleotides as long as it can reduce or lose the Sre1 expression. Examples of deletion of nucleotides include deletion of a part of the transcriptional region, preferably 10 nucleotides or more, more preferably 20 nucleotides or more, even more preferably 100 nucleotides or more, even preferably 200 nucleotides or more, even more preferably the whole of the transcriptional region. Examples of substitution of nucleotides include substitution of nucleotides within a range from the 5' end of the transcriptional region to the 150th nucleotide, preferably to the 100th nucleotide, more preferably to the 50th nucleotide, even more preferably to the 30th nucleotide, even more preferably the 20th nucleotide with a nonsense codon or with a control region that can reduce the Sre1 expression. Examples of insertion of nucleotides include addition of 50 or more nucleotides, preferably 100 or more nucleotides, more preferably 200 or more nucleotides, even more preferably 500 or more nucleotides, even more preferably a DNA fragment of 1 kb or more at the position following the nucleotides within a range from the 5' end of the transcriptional region to the 150th nucleotide, preferably to the 100th nucleotide, more preferably to the 50th nucleotide, even more preferably to the 30th nucleotide, even more preferably to the 20th nucleotide. Preferred examples of the form of the addition of nucleotides include introduction of a drug resistance gene, such as a hygromycin resistance gene and an aureobasidin resistance gene, or an auxotrophic gene, such as an acetoamidase gene that is not possessed by the filamentous fungi.

The method of introducing a nucleotide mutation into the sre1 gene on the chromosomal DNA of filamentous fungi may be, for example, a method of using homologous recombination. In a method of using common homologous recombination, for example, a gene mutated by deletion, substitution, or insertion of nucleotides is inserted between the upstream region and the downstream region of the sre1 gene to produce a DNA fragment including a drug resistance gene or an auxotrophic gene, and the DNA fragment is used to cause homologous recombination in the locus of the sre1 gene of a host cell to which nucleotide deletion or the like is desired to be introduced.

In the method using homologous recombination, specifically, i) the DNA fragment for homologous recombination is introduced into a filamentous fungus parent strain by a usual manner, and subsequently a transformant into which, as a result of homologous recombination, a plasmid for homologous recombination has been introduced on the chromosomal DNA is selected using drug resistance or auxotrophy as an index; ii) PCR is performed using the chromosomal DNA of the resulting transformant as a template. The primers on this occasion are designed such that the site where the nucleotides of the gene have been deleted, substituted, or inserted is amplified. A strain in which a gene having the original length is not amplified, but a gene having a length reflecting the deletion, substitution, or insertion of the nucleotides is amplified is selected; and iii) finally, a strain in which the mutated gene is introduced into only the locus of the chromosomal DNA, but not introduced into any another site can be obtained by Southern analysis.

Alternatively, a nucleotide mutation may be introduced into the sre1 gene on the chromosomal DNA of a parent strain by, for example, a method using a bacteriophage or conjugation.

The filamentous fungus mutant strain of the present invention can also be obtained by subjecting a filamentous fungus parent strain to mutation processing and then selecting a strain in which Sre1 expression is reduced compared to the parent strain or is lost. Examples of the mutation processing include treatment with N-methyl-N'-nitro-N-nitrosoguanidine (NTG), ethylnitrosourea, or ultraviolet light (Shinban Biseibutsu Zikken-ho (New Edition, Microorganisms Experimental Methods), 1999, pp. 126-134, Kodansha Scientific Ltd.), and irradiation with radioactive rays. In addition, a variety of alkylating agents and carcinogens can be used as mutagens.

Alternatively, the Sre1 expression can be reduced without introducing a mutation into the sre1 gene. Examples of such a method include introduction of a nucleic acid having an activity of degrading a transcriptional product of a gene encoding a protein or a nucleic acid suppressing translation of the transcriptional product into a protein. Examples of such a nucleic acid include a nucleic acid having a nucleotide sequence complementary or substantially complementary to the nucleotide sequence of mRNA encoding the protein or a part of the nucleotide sequence.

A nucleotide sequence substantially complementary to the nucleotide sequence of mRNA encoding Sre1 refers to a nucleotide sequence having complementarity such that the nucleotide sequence binds to the target sequence of the mRNA to inhibit the translation thereof under physiological conditions inside the target filamentous fungus cells, and specifically, for example, a nucleotide sequence having an identity of about 80% or more, preferably about 90% or more, more preferably about 95% or more, even more preferably about 97% or more with the nucleotide sequence completely complementary to the nucleotide sequence of the mRNA (i.e., the nucleotide sequence of a complementary strand of the mRNA) in the overlapping region.

More specifically, examples of the nucleotide sequence complementary or substantially complementary to the nucleotide sequence of mRNA encoding Sre1 include polynucleotides in the above-described (d) to (i).

Preferred examples of the mRNA encoding Sre1 include mRNA encoding Sre1 of *Trichoderma reesei* having the nucleotide sequence represented by SEQ ID NO: 1.

"A part of the nucleotide sequence complementary or substantially complementary to the nucleotide sequence of mRNA encoding Sre1" may have no limitation of length and position as long as it can specifically binds to mRNA of Sre1 and can inhibit the translation of the mRNA into the protein. From the viewpoint of sequence specificity, the part complementary or substantially complementary to the target sequence includes at least 10 or more nucleotides, preferably about 15 or more nucleotides, more preferably about 20 or more nucleotides.

Specifically, preferred examples of the nucleic acid having a nucleotide sequence complementary or substantially complementary to the nucleotide sequence of mRNA encoding Sre1 or a part of the nucleotide sequence includes the following (j) to (l):

(j) Antisense RNA to mRNA encoding Sre1;
(k) Small interfering RNA (siRNA) to mRNA encoding Sre1; and
(l) Ribozyme to mRNA encoding Sre1.

The parent strain in the present invention is not limited as long as it is a filamentous fungus that expresses Sre1 and has cellulase activity and/or xylanase activity, and examples thereof include filamentous fungi belonging to Eumycota or Oomycota. Specifically, the filamentous fungi are, for example, those belonging to *Trichoderma, Aspergillus, Penicillium, Neurospora, Fusarium, Chrysosporium, Humicola, Emericella*, or *Hypocrea*. The filamentous fungi are preferably those belonging to *Trichoderma*.

Examples of the filamentous fungi belonging to *Trichoderma* include *Trichoderma reesei, Trichoderma longibrachiatum, Trichoderma harzianum, Trichoderma koningii*, and *Trichoderma viride*. The filamentous fungi are preferably *Trichoderma reesei*, more preferably *Trichoderma reesei* PCD-10 strain (FERM P-8172).

The filamentous fungi as the parent strain may be a wild-type strain, a strain artificially bred from the wild-type strain, or a variant strain (variant) or a mutant in which a nucleotide sequence in the genome is substituted, added, deleted, or modified.

Preferred examples of the filamentous fungus mutant strain of the present invention include filamentous fungi obtained by deleting the sre1 gene of the *Trichoderma reesei* PCD-10 strain (FERM P-8172) by homologous recombination to lose the Sre1 expression. Specifically, *Trichoderma reesei* ΔSre1 disclosed in Example described below is an example.

In the thus-constructed filamentous fungus mutant strain of the present invention, the Sre1 expression in the cells is lost or reduced compared to the parent strain, and therefore the inhibition of production of cellulase or xylanase by glucose is consequently suppressed compared to the parent strain.

Accordingly, a reduction in productivity of a cellulase or a xylanase can be suppressed by using the filamentous fungus mutant strain of the present invention, even if a high concentration of glucose is present in the culture medium.

<Production of Cellulase and/or Xylanase>

A cellulase and/or a xylanase can be produced by culturing the filamentous fungus mutant strain of the present invention in the presence of a cellulase inducer to generate and accumulate a cellulase and/or a xylanase in a culture product and collecting the cellulase and/or the xylanase from the culture product.

Herein, the "cellulase inducer" is not limited as long as it is a substance that induces the production of cellulase by cellulase-producing filamentous fungi and is, for example, a compound selected from cellulose; sophorose; and cellooligosaccharides, such as cellobiose, cellotriose, cellotetraose, cellopentaose, and cellohexaose.

Herein, the cellulose encompasses a polymer of glucose polymerized by β-1,4-glucoside bonds and derivatives thereof. The degree of polymerization of glucose is not particularly limited. Examples of the derivative include carboxymethylated, aldehyded, and esterified derivatives. Furthermore, the cellulose may be β glucoside, which is a glycoside; lignocellulose, which is a complex with lignin and/or hemicellulose; or a complex with, for example, pectin. The cellulose may be crystalline cellulose or may be amorphous cellulose.

The cellulase inducer can be added by any method, such as one-shot addition (batch method), divided addition (fed-batch method), or continuous addition (feeding method). The cellulase inducer may be added to a culture medium at any amount that can induce production of a cellulase and/or a xylanase by the filamentous fungi mutant strain of the present invention. The amount differs depending on the method of addition, but the total amount is preferably 0.1 mass % or more, more preferably 0.5 mass % or more, even more preferably 1 mass % or more and preferably 40 mass % or less, more preferably 35 mass % or less, even more preferably 30 mass % or less of the amount of the culture medium. The amount is preferably from 0.1 to 40 mass %, more preferably from 0.5 to 35 mass %, even more preferably from 1 to 30 mass %.

Among the above-mentioned methods, the amount of the cellulase inducer in the one-shot addition is preferably 0.1 mass % or more, more preferably 0.5 mass % or more, even more preferably 1 mass % or more and preferably 16 mass % or less, more preferably 14 mass % or less, even more preferably 12 mass % or less. The amount is preferably from 0.1 to 16 mass %, more preferably from 0.5 to 14 mass %, even more preferably from 1 to 12 mass %.

The culture medium used in the method of the present invention may be a synthetic culture medium or a natural culture medium that contains nutrients necessary for proliferation of the filamentous fungus mutant strain of the present invention and production of a cellulase and/or a xylanase, such as a carbon source, a nitrogen source, inorganic salts, and vitamins.

The carbon source may be any carbon source that can be assimilated by the filamentous fungus mutant strain of the present invention, and examples thereof include carbohydrates, such as glucose and fructose; alcohols, such as ethanol and glycerol; and organic acids, such as acetic acid, in addition to the above-mentioned cellulase inducers. These carbon sources may be used alone or in combination of two or more thereof.

In the filamentous fungus mutant strain of the present invention, the productivity of a cellulase or a xylanase is not suppressed even when glucose is present in the culture medium at the time of starting the culture. In this case, the amount of glucose added is preferably 0.1 mass % or more, more preferably 0.5 mass % or more, even more preferably 2.5 mass % or more and 15 mass % or less, more preferably 10 mass % or less, even more preferably 5 mass % or less of the amount of the culture medium. The amount is preferably from 0.1 to 15 mass %, more preferably from 0.5 to 10 mass %, more preferably from 2.5 to 5 mass %. The mass ratio of the amounts of the cellulase inducer and glucose in the culture medium is preferably from 10:1 to 1:1, more preferably from 4:1 to 2:1.

Examples of the nitrogen source include ammonium salts, such as ammonia and ammonium sulfate; nitrogen compounds, such as amine; natural nitrogen sources, such as peptone and soybean hydrolysates.

Examples of the inorganic salt include potassium phosphate, magnesium sulfate, sodium chloride, ferrous sulfate, and potassium carbonate.

Examples of the vitamin include biotin and thiamine. The medium can further optionally contain a substance required for growth of the filamentous fungi mutant strain of the present invention.

The culture is preferably performed under aerobic conditions such as shaking culture or aerated and agitated culture. The culture temperature is preferably 10° C. or more, more preferably 20° C. or more, even more preferably 25° C. or more and preferably 50° C. or less, more preferably 42° C. or less, even more preferably 35° C. or less. The temperature is preferably from 10° C. to 50° C., more preferably from 20° C. to 42° C., even more preferably from 25° C. to 35° C.

The pH in the culture is from 3 to 9, preferably from 4 to 5. The culture time is from 10 hours to 10 days, preferably from 2 to 7 days.

After the completion of the culture, the culture product is collected, is subjected to cell disruption by, for example, ultrasonication or pressurization, as needed, and is solid-liquid separated by, for example, filtration or centrifugation, followed by an appropriate combination of ultrafiltration, salting-out, dialysis, chromatography, and so on to obtain a cellulase and/or a xylanase. The degree of separation and purification is not particularly limited. The culture supernatant or its roughly separated and purified product itself can also be used as a cellulase or a xylanase.

In the present invention, the term "cellulase" is a generic name of enzymes degrading cellulose and encompasses endoglucanase (EC 3.2.1.4) cleaving cellulose from the inside of the molecule; and exoglucanase (cellobiohydrolase, EC 3.2.1.91) and β-glucosidase (EC 3.2.1.21) degrading cellulose from the reducing terminal or nonreducing terminal to release cellobiose.

The "xylanase" is an enzyme (EC 3.2.1.8) hydrolyzing the β1-4 bond of xylan to generate xylose.

Degradation or saccharification of cellulose or xylan and production of a monosaccharide using the filamentous fungus mutant strain of the present invention can be performed by known methods.

That is, a monosaccharide can be produced by using the above-mentioned culture product, obtained by culturing the filamentous fungus mutant strain of the present invention in the presence of a cellulase inducer, as a biomass saccharifying agent and heating the culture product together with a cellulose- or xylan-containing material (biomass) in an aqueous solvent with stirring or shaking to degrade or saccharify the biomass.

As the cellulose- or xylan-containing material, those exemplified as the cellulase inducers to be contained in the above-described culture medium can be used.

In the degradation or saccharification of biomass, the reaction solution may have any pH and any temperature within ranges that do not inactivate the cellulase or xylanase. Generally, when the reaction is performed at normal pressure, the temperature is within a range of 5° C. to 95° C., and the pH is within a range of 1 to 11.

The process of degradation or saccharification of biomass may be a batch system or a continuous system.

Regarding the above-described embodiments, the present invention further discloses the following aspects:

<1> A filamentous fungus mutant strain wherein Sre1 expression is reduced compared to a parent strain or is lost;

<2> The filamentous fungus mutant strain according to aspect <1>, wherein the Sre1 expression is lost;

<3> The filamentous fungus mutant strain according to aspect <1>, wherein the Sre1 is a protein selected from the group consisting of the following (a) to (c):
(a) a protein having the amino acid sequence represented by SEQ ID NO: 2,
(b) a protein having an amino acid sequence with an identity of 80% or more with the amino acid sequence represented by SEQ ID NO: 2 and having an activity as a transcription factor for genes encoding cholesterol synthesis enzymes, and
(c) a protein having the amino acid sequence represented by SEQ ID NO: 2 in which one to several amino acids are deleted, substituted, added-or inserted and having an activity as a transcription factor for genes encoding cholesterol synthesis enzymes;

<4> The filamentous fungus mutant strain according to any of aspects <1> to <3>, wherein sre1 gene is deleted or inactivated;

<5> The filamentous fungus mutant strain according to aspect <4>, wherein the sre1 gene is represented by any of the following (d) to (i):
(d) a polynucleotide having the nucleotide sequence represented by SEQ ID NO: 1,
(e) a polynucleotide having a nucleotide sequence with an identity of 80% or more with the nucleotide sequence represented by SEQ ID NO: 1 and encoding a protein having an activity as a transcription factor for genes encoding cholesterol synthesis enzymes,
(f) a polynucleotide hybridizing to a complementary strand of the polynucleotide having the nucleotide sequence represented by SEQ ID NO: 1 under stringent conditions and encoding a protein having an activity as a transcription factor for genes encoding cholesterol synthesis enzymes,
(g) a polynucleotide encoding a protein having the amino acid sequence represented by SEQ ID NO: 2,
(h) a polynucleotide encoding a protein having the amino acid sequence represented by SEQ ID NO:2 in which one to several amino acids are deleted, substituted, added or inserted and having an activity as a transcription factor for genes encoding cholesterol synthesis enzymes, and
(i) a polynucleotide encoding a protein having an amino acid sequence with an identity of 80% or more with the amino acid sequence represented by SEQ ID NO: 2 and having an activity as a transcription factor for genes encoding cholesterol synthesis enzymes;

<6> The filamentous fungus mutant strain according to any one of aspects <1> to <5>, wherein the filamentous fungus belongs to Trichoderma;

<7> The filamentous fungus mutant strain according to any of aspects <1> to <5>, wherein the filamentous fungus is Trichoderma reesei;

<8> A method of producing a cellulase and/or a xylanase, the method comprising a step of culturing the filamentous fungus mutant strain according to any one of aspects <1> to <7> in the presence of a cellulase inducer to generate and accumulate a cellulase and/or a xylanase in a culture product and a step of collecting the cellulase and/or the xylanase from the culture product;

<9> A method of producing a cellulase and/or a xylanase, the method comprising a step of culturing the filamentous fungus mutant strain according to any of aspects <1> to <7> in the presence of a cellulase inducer and glucose to generate and accumulate a cellulase and/or a xylanase in a culture product and a step of collecting the cellulase and/or the xylanase from the culture product;

<10> The method of producing a cellulase and/or a xylanase according to aspect <9>, wherein the culture medium comprises the cellulase inducer in an amount of from 0.1 to 40 mass %, preferably from 0.5 to 35 mass %, more preferably from 1 to 30 mass in total, and glucose in an amount of from 0.1 to 15 mass %, preferably from 0.5 to 10 mass %, more preferably 2.5 to 5 mass %;

<11> The method of producing a cellulase and/or a xylanase according to aspect <10>, wherein a mass ratio of the cellulase inducer and glucose is from 10:1 to 1:1, preferably from 4:1 to 2:1;

<12> A method of producing a saccharide from biomass, the method comprising using a culture product, obtained by culturing the filamentous fungus mutant strain according to any of aspects <1> to <7> in the presence of a cellulase inducer, as a biomass saccharifying agent; and <13> A method of saccharifying biomass, the method comprising using a culture product, obtained by culturing the filamentous fungus mutant strain according to any of aspects <1> to <7> in the presence of a cellulase inducer, as a biomass saccharifying agent.

EXAMPLES

The present invention will now be described more specifically by Examples.

Example 1

Gene Mutation Site Analysis

Trichoderma reesei PCD-10 strain was used as a parent strain and subjected to mutation processing, and a strain in which cellulase production in the presence of glucose was increased compared to the parent strain was selected. The genomic DNA of this mutant strain was extracted with an ISOPLANT II DNA extraction kit (Nippon Gene Co., Ltd.) and was subjected to comparative genomic analysis with Trichoderma reesei PCD-10 strain. The results demonstrated that mutation was introduced into the ORF of the sre1 gene and gene disruption due to frameshift was consequently caused.

Example 2

Production of Gene Disruption Strain (1) Construction of Plasmid DNA for Gene Disruption Using a plasmid pUC-Sre1 carrying a part of the sre1 gene derived from Trichoderma reesei (SEQ ID NO: 3) inserted into the HincII restriction endonuclease cutting site of pUC118 (Takara Bio Inc.) as a template and using forward primer 1 (SEQ ID NO: 4) and reverse primer 1 (SEQ ID NO: 5) shown in Table 1, PCR was carried out to amplify a fragment (A) of about 5.2 kbp. Separately, using an acetamidase amdS derived from Aspergillus nidulans (SEQ ID NO: 6) as a template and using forward primer 2 (SEQ ID NO: 7) and reverse primer 2 (SEQ ID NO: 8) shown in Table 1, PCR was carried out to amplify a fragment (B) of about 3.1 kbp. The resulting DNA fragments (A) and (B) were treated in accordance with the protocol of In-Fusion HD Cloning Kit (Takara Bio Inc.) to construct a plasmid carrying amdS gene inserted into the sre1 gene. This plasmid was transformed into *E. coli* DH5α competent Cells (Takara Bio Inc.), and a strain retaining the plasmid carrying the target gene was selected from the transformants obtained as ampicillin resistance strains by colony PCR. The selected transformant was cultured (at 37° C. for 1 day) using an ampicillin-containing LB medium, and the plasmid was then collected from the resulting cells and purified with High Pure Plasmid Isolation kit (Roche Diagnostics K.K.). Herein, the resulting vector is referred to as pUC-Sre1-amdS.

(2) Production of Transformant

*Trichoderma reesei* PCD-10 strain was transformed with the vector constructed in the above (1). The introduction was performed by a protoplast PEG method (Biotechnol Bioeng. 2012, January. 109(1): 92-99). The transformant was selected with a selection medium (2% glucose, 1.1 M sorbitol, 2% agar, 0.2% $KH_2PO_4$ (pH 5.5), 0.06% $CaCl_2.2H_2O$, 0.06% $CsCl_2$, 0.06% $MgSO_4.7H_2O$, 0.06% acetamide, 0.1% Trace element1, wherein every "%" means w/v %) containing acetamide as a single nitrogen source. Trace element 1 has the following composition: 0.5 g $FeSO_4.7H_2O$, 0.2 g $CoCl_2$, 0.16 g $MnSO_4.H_2O$, and 0.14 g $ZnSO_4.7H_2O$ were diluted with distilled water to 100 mL total. Among the resulting transformants, a transformant having gene disruption by insertion of amdS into the sre1 gene site by homologous recombination was selected by colony PCR using primers: forward primer 3 (SEQ ID NO: 9) and reverse primer 3 (SEQ ID NO: 10) and forward primer 4 (SEQ ID NO: 11) and reverse primer 4 (SEQ ID NO: 12), shown in Table 1. A strain showing correct DNA amplification was defined as a transformant, and the strain obtained herein was referred to as PCD-10ΔSre1.

TABLE 1

| Primer | Sequence | SEQ ID NO |
|---|---|---|
| Forward primer 1 | CGTTTCCAGTGCGCATTACCGGAGGAGATTCCGAG | 4 |
| Reverse primer 1 | CCAATGATGTGCGCAGGCAATGTTTCTCAGTTGTT | 5 |
| Forward primer 2 | TGCGCACATCATTGGATAGG | 7 |
| Reverse primer 2 | TGCGCACTGGAAACGCAACC | 8 |
| Forward primer 3 | ATCCCTCCCCCATCGTCGCA | 9 |
| Reverse primer 3 | TCCTGACCCTCCATGCTGTTCGCCATCTTT | 10 |
| Forward primer 4 | CCAGTCCGAGTCGGACA | 11 |
| Reverse primer 4 | CATTGTATGCCTGATACCAC | 12 |

Example 3

Culture of Transformant

The enzyme productivity of a transformant was evaluated by the following culture. For pre-culture, spores of *Trichoderma reesei* PCD-10 strain (WT) and PCD-10ΔSre1 produced in Example 1 were each inoculated at $1 \times 10^5$ cells/mL in 50 mL of a culture medium placed in a 500-mL flask and were shaking-cultured at 28° C. and at 220 rpm (PRXYg-98R manufactured by Preci Co., Ltd.). The composition of the medium was as follows: 1% glucose, 0.14% $(NH_4)_2SO_4$, 0.2% $KH_2PO_4$, 0.03%, $CaCl_2.2H_2O$, 0.03% $MgSO_4.7H_2O$, 0.1% hipolypepton N, 0.05% Bacto Yeast extract, 0.1% Tween 80, 0.1% Trace element 2, and 50 mM tartaric acid buffer (pH 4.0). The composition of Trace element 2 was as follows: 6 mg $H_3BO_3$, 26 mg $(NH_4)_6Mo_7O_{24}.4H_2O$, 100 mg $FeCl_3.6H_2O$, 40 mg $CuSO_4.5H_2O$, 8 mg $MnCl_2.4H_2O$, and 200 mg $ZnCl_2$ were diluted with distilled water to 100 mL total. After the pre-culture for 2 days, main culture was performed using a jar fermentor (manufactured by Biott Corporation, BTR-25NA1S-8M). Ten percent (v/v %) of the pre-culture solution was inoculated and was cultured for 5 days. The carbon source was 10% Avicel or 10% Avicel+5% glucose, and other culture medium components were as follows: 0.42% $(NH_4)_2SO_4$, 0.2% $KH_2PO_4$, 0.03% $CaCl_2.2H_2O$, 0.03% $MgSO_4.7H_2O$, 0.1% hipolypepton N, 0.05% Bacto Yeast extract, 0.1% Tween 80, 0.1% Trace element 2, and 0.2% Antifoam PE-L. The jar fermentor was set as follows: a temperature of 28° C., an air flow rate of 0.5 vvm, and a pH of 4.5 (adjusted with 5% ammonia water). The agitation rate was varied to maintain a constant DO of 3.0 ppm. The main culture was performed for 5 days.

Example 4

Measurement of Protein Concentration

The concentration of a protein was measured by a Bradford method. In the Bradford method, Quick Start Protein Assay (Bio-Rad Laboratories, Inc.) was used, and the protein amount was calculated based on a standard curve drawn using bovine γ-globulin as a standard protein.

The results demonstrated that the reduction in enzyme productivity was suppressed in the produced transformant compared to a parent strain even if glucose was present at a high concentration.

What is claimed is:

1. A filamentous fungus mutant strain wherein Sre1 expression is reduced compared to its parent strain or is lost, wherein the filamentous fungus is Trichoderma and wherein Sre1 is a protein selected from the group consisting of the following (a) to (c):
   (a) a protein having the amino acid sequence of SEQ ID NO: 2;
   (b) a protein having an amino acid sequence with an identity of 80% or more with the amino acid sequence of SEQ ID NO: 2 and having an activity as a transcription factor for genes encoding cholesterol synthesis enzymes; and
   (c) a protein having the amino acid sequence of SEQ ID NO: 2 but in which one to 12 amino acids are deleted, substituted, added or inserted and having an activity as a transcription factor for genes encoding cholesterol synthesis enzymes.

2. The filamentous fungus mutant strain according to claim 1, wherein the Sre1 expression is lost.

3. The filamentous fungus mutant strain according to claim 1, wherein the sre1 gene is deleted or inactivated.

4. The filamentous fungus mutant strain according to claim 3, wherein the sre1 gene comprises any of the following (d) to (i):
   (d) a polynucleotide having the nucleotide sequence of SEQ ID NO: 1;
   (e) a polynucleotide having a nucleotide sequence with an identity of 80% or more with the nucleotide sequence of SEQ ID NO: 1 and encoding a protein having an activity as a transcription factor for genes encoding cholesterol synthesis enzymes;
   (f) a polynucleotide hybridizing to a complementary strand of the polynucleotide having the nucleotide sequence of SEQ ID NO: 1 under stringent conditions and encoding a protein having an activity as a transcription factor for genes encoding cholesterol synthesis enzymes;
   (g) a polynucleotide encoding a protein having the amino acid sequence of SEQ ID NO: 2;
   (h) a polynucleotide encoding a protein having the amino acid sequence of SEQ ID NO: 2 but in which one to 12 amino acids are deleted, substituted, added or inserted and having an activity as a transcription factor for genes encoding cholesterol synthesis enzymes; and
   (i) a polynucleotide encoding a protein having an amino acid sequence with an identity of 80% or more with the amino acid sequence of SEQ ID NO: 2 and having an activity as a transcription factor for genes encoding cholesterol synthesis enzymes.

5. The filamentous fungus mutant strain according to claim 1, wherein the Trichoderma is Trichoderma reesei, Trichoderma longibrachiatum, Trichoderma harzianum, Trichoderma koningii, or Trichoderma viride.

6. A method of producing a cellulase and/or a xylanase, the method comprising a step of culturing the filamentous fungus mutant strain according to claim 1 in the presence of a cellulase inducer to generate and accumulate a cellulase and/or a xylanase in a culture product and a step of collecting the cellulase and/or the xylanase from the culture product.

7. A method of producing a cellulase and/or a xylanase, the method comprising a step of culturing the filamentous fungus mutant strain according to claim 1 in the presence of a cellulase inducer and glucose to generate and accumulate a cellulase and/or a xylanase in a culture product and a step of collecting the cellulase and/or the xylanase from the culture product.

8. The method of producing a cellulase and/or a xylanase according to claim 7, wherein the culture medium comprises the cellulase inducer in an amount of from 0.1 to 40 mass % in total and glucose in an amount of from 0.5 to 10 mass %.

9. The method of producing a cellulase and/or a xylanase according to claim 8, wherein the mass ratio of the cellulase inducer and glucose is 10:1 to 1:1.

10. A method of producing a saccharide from biomass, the method comprising using a culture product, obtained by culturing the filamentous fungus mutant strain according to claim 1 in the presence of a cellulase inducer, as a biomass saccharifying agent.

11. A method of saccharifying biomass, the method comprising using a culture product, obtained by culturing the filamentous fungus mutant strain according to claim 1 in the presence of a cellulase inducer, as a biomass saccharifying agent.

12. The filamentous fungus mutant strain of claim 1, wherein the Sre1 protein is a protein having the amino acid sequence of SEQ ID NO: 2.

13. The filamentous fungus mutant strain of claim 1, wherein the Sre1 protein is a protein having an amino acid sequence with an identity of 80% or more with the amino acid sequence of SEQ ID NO: 2 and having an activity as a transcription factor for genes encoding cholesterol synthesis enzymes.

14. The filamentous fungus mutant strain of claim 1, wherein the Sre1 protein is a protein having the amino acid sequence of SEQ ID NO: 2 but in which one to 12 amino acids are deleted, substituted, added or inserted and having an activity as a transcription factor for genes encoding cholesterol synthesis enzymes.

15. The filamentous fungus mutant strain according to claim 4, wherein the sre1 gene is a polynucleotide having the nucleotide sequence of SEQ ID NO: 1.

16. The filamentous fungus mutant strain according to claim 4, wherein the sre1 gene is a polynucleotide having a nucleotide sequence with an identity of 80% or more with the nucleotide sequence of SEQ ID NO: 1 and encoding a protein having an activity as a transcription factor for genes encoding cholesterol synthesis enzymes.

17. The filamentous fungus mutant strain according to claim 4, wherein the sre1 gene is a polynucleotide hybridizing to a complementary strand of the polynucleotide having the nucleotide sequence of SEQ ID NO: 1 under stringent conditions and encoding a protein having an activity as a transcription factor for genes encoding cholesterol synthesis enzymes.

18. The filamentous fungus mutant strain according to claim 4, wherein the sre1 gene is a polynucleotide encoding a protein having the amino acid sequence of SEQ ID NO: 2.

19. The filamentous fungus mutant strain according to claim 4, wherein the sre1 gene is a polynucleotide encoding a protein having the amino acid sequence of SEQ ID NO: 2 but in which one to 12 amino acids are deleted, substituted, added or inserted and having an activity as a transcription factor for genes encoding cholesterol synthesis enzymes.

20. The filamentous fungus mutant strain according to claim 4, wherein the sre1 gene is a polynucleotide encoding a protein having an amino acid sequence with an identity of 80% or more with the amino acid sequence of SEQ ID NO: 2 and having an activity as a transcription factor for genes encoding cholesterol synthesis enzymes.

* * * * *